(12) United States Patent
Van Sciver et al.

(10) Patent No.: US 8,679,573 B2
(45) Date of Patent: Mar. 25, 2014

(54) STENT COATING METHOD AND APPARATUS

(75) Inventors: Jason Van Sciver, Los Gatos, CA (US); Greg Teaby, Sunnyvale, CA (US); Phil Foreman, San Jose, CA (US); Manish Gada, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 2592 days.

(21) Appl. No.: 11/478,151

(22) Filed: Jun. 28, 2006

(65) Prior Publication Data
US 2008/0003349 A1 Jan. 3, 2008

(51) Int. Cl.
C23C 16/52 (2006.01)
B05C 11/00 (2006.01)
B05D 5/12 (2006.01)

(52) U.S. Cl.
USPC .............. 427/8; 427/2.1; 427/2.14; 427/2.28; 427/9; 427/10; 427/258; 347/68; 118/679; 118/713

(58) Field of Classification Search
USPC .................. 427/2.1, 2.14, 2.28, 8, 9, 10, 258; 347/68; 118/679, 713
See application file for complete search history.

(56) References Cited

U.S. PATENT DOCUMENTS

2001/0050294 A1 12/2001 Plattner et al.
2006/0172060 A1* 8/2006 Teichman et al. ................. 427/8

FOREIGN PATENT DOCUMENTS

| WO | WO 99/62074 | 12/1999 |
| WO | WO 03/092909 | 11/2003 |
| WO | WO 2006/012034 | 2/2006 |
| WO | WO 2006/079926 | 8/2006 |
| WO | WO 2007/045994 | 4/2007 |

OTHER PUBLICATIONS

Invitation to Pay Additional Fees for PCT/US2007/011291, filed May 9, 2007, mailed Oct. 30, 2007, 7 pgs.

* cited by examiner

*Primary Examiner* — Brian P Mruk
(74) *Attorney, Agent, or Firm* — Squire Sanders (US) LLP

(57) ABSTRACT

An apparatus includes a piezoelectric print head capable of ejecting a droplet of a coating substance towards a stent strut, a sensor capable of sensing a parameter of the droplet, and a controller, communicatively coupled to the print head and the sensor, capable of determining if the parameter of the droplet meets a requirement. A method includes ejecting a droplet of a coating substance towards a stent strut with a piezoelectric print head, sensing a parameter of the droplet, and determining whether the parameter of the droplet meets a requirement.

26 Claims, 9 Drawing Sheets

STENT COATING METHOD AND APPARATUS

TECHNICAL FIELD

This invention relates to a method and apparatus for coating a stent surface.

BACKGROUND

In the last several years, minimally invasive surgical procedures, such as percutaneous transluminal coronary angioplasty (PTCA), have become increasingly common. A PTCA procedure involves the insertion of a catheter into a coronary artery to position an angioplasty balloon at the site of a stenotic lesion that is at least partially blocking the coronary artery. The balloon is then inflated to compress the stenosis and to widen the lumen to allow an efficient flow of blood through the coronary artery.

Following PTCA and other stenotic treatment procedures, a significant number of patients experience restenosis or other vascular blockage problems. These problems are prone to arise at the site of the former stenosis.

In order to help avoid restenosis and other similar problems, a stent may be implanted into the vessel at the site of the former stenosis with a stent delivery catheter. Stents are described in U.S. Pat. No. 4,733,665 to Palmaz, U.S. Pat. No. 4,800,882 to Gianturco, and U.S. Pat. No. 4,886,062 to Wiktor.

FIG. 1 illustrates a conventional stent 10 formed from radially expandable struts 12 that are interconnected by connecting elements 14. Lateral openings or gaps 16 are formed between adjacent struts 12. The struts 12 and the connecting elements 14 define a tubular stent body having an outer, tissue-contacting (abluminal) surface and an inner (luminal) surface.

Stents can also be used to deliver drugs locally. Local delivery is often preferred over systemic delivery, particularly where high systemic doses are necessary to affect a particular site. High systemic doses of drugs often create adverse effects. For example, following angioplasty, radiotherapy and drug delivery treatments applied to the former stenosis have been found to aid in the healing process and to reduce significantly the risk of restenosis and other similar problems. One proposed method of local delivery is to coat a stent surface with one or more drugs.

There are several conventional methods for coating a stent with a drug, e.g. by dipping the stent in a coating substance containing the drug or by spraying the solution onto the stent. Dipping and spraying usually results in completely coating all stent surfaces, i.e., both luminal and abluminal surfaces. While the coating on the abluminal surface provides an advantageous direct delivery of the drug to the site of the former stenosis, the coating on the luminal surface can be washed away by the blood, which in some cases makes it therapeutically insignificant.

Moreover, the luminal surface coating often detrimentally affects stent deliverability and the coating's mechanical integrity. The luminal coating may increase the friction coefficient of the stent's surface, making withdrawal of a deflated balloon more difficult. The coating may also adhere to the balloon. Consequently, balloon deflation and withdrawal may damage the coating or remove portions of the coating from the stent, resulting in a thrombogenic stent surface and embolic debris.

The dipping and spraying methods have additional shortcomings. For example, these methods tend to cause webbing between adjacent stent struts and coating pools on the stent, making it difficult to control the amount of drug coated on the stent. Additionally, the spraying method may cause coating defects at the stent-stent-mandrel interface. Upon removal from the stent mandrel, the coating material at the interface may detach from the stent, leaving uncoated stent areas.

To overcome the above shortcomings, piezoelectric delivery systems have been developed, which deliver coating droplets to specific stent surfaces, allowing a more precise coating of the stent. However, these systems also have several drawbacks. For example, they do not consider several factors that affect droplet size (or volume). For example, the droplet size is affected by the coating substance's viscosity or density. The higher the viscosity or density, the smaller the droplet size. In addition, nozzle clogging also affects droplet size. As a result, these conventional piezoelectric delivery systems cannot precisely control the delivery rate of coating substance.

SUMMARY

The present invention provides a method and apparatus that can monitor the size (diameter or volume) of droplets generated by a piezoelectric delivery system and adjust system parameters to maintain a desired droplet size. The invention can be used also for other purposes. For example, the method and apparatus can be additionally or alternatively used to monitor and control a droplet's alignment with a stent strut, allowing a precise delivery of coating substance to a specific stent surface. Moreover, the method and apparatus can be used to monitor and control droplet velocity. Further, the method and apparatus can be used to monitor and control "drop mode" to ensure that a "single drop mode" has been achieved and there are no undesirable "satellite" droplets.

According to one aspect of the invention, a method includes the steps of ejecting a droplet of a coating substance towards a stent strut with a print head of a piezoelectric delivery system; sensing a parameter of the droplet; and determining whether the parameter of the droplet meets a requirement. The sensed droplet parameter may be droplet size, droplet velocity, the droplet's alignment with a stent strut, and/or the drop mode.

According to another aspect of the invention, an apparatus includes a piezoelectric print head, a sensor and a controller. The piezoelectric print head can eject a droplet of a coating substance. The sensor can sense a parameter of the droplet. The controller is communicatively coupled to the print head and the sensor, and can determine whether the parameter of the droplet meets a requirement.

The sensing step may be carried out by an imaging device, such as a camera, which provides an image of the droplet. From the image, the droplet parameter can be determined. The droplet may be illuminated to provide a clear image, preferably by a strobe light.

The piezoelectric print head may be controlled to adjust the droplet parameter to meet the requirement. For example, the ejecting power of the print head may be controlled. More specifically, one or more of the pulse width, pulse magnitude, pulse frequency, and ejection frequency of the print head may be controlled. Furthermore, the stent position or print head position may be adjusted based on the droplet parameter.

The present invention has several advantages over the prior art. For example, the present invention delivers a precisely-controlled amount of coating to a stent surface. This is accomplished by monitoring droplet parameters, such as droplet size, droplet velocity, droplet mode, and/or the droplet's alignment with the stent strut, and by controlling the piezoelectric print head to maintain the droplet parameters at desired values.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 1:
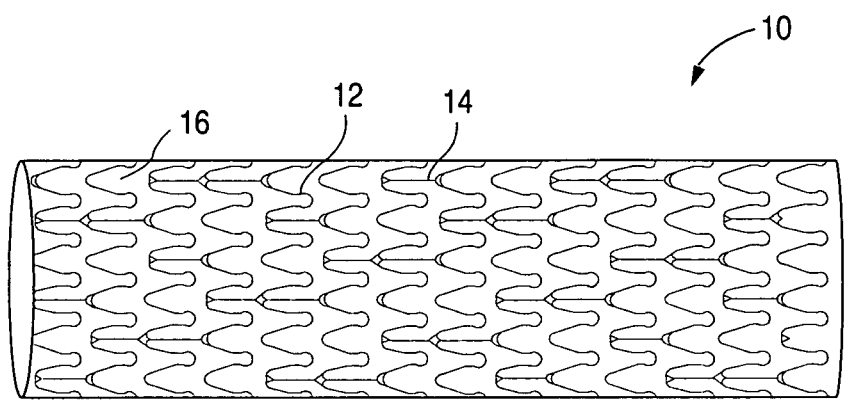
FIG. 1 illustrates a conventional stent.
Figure 2:
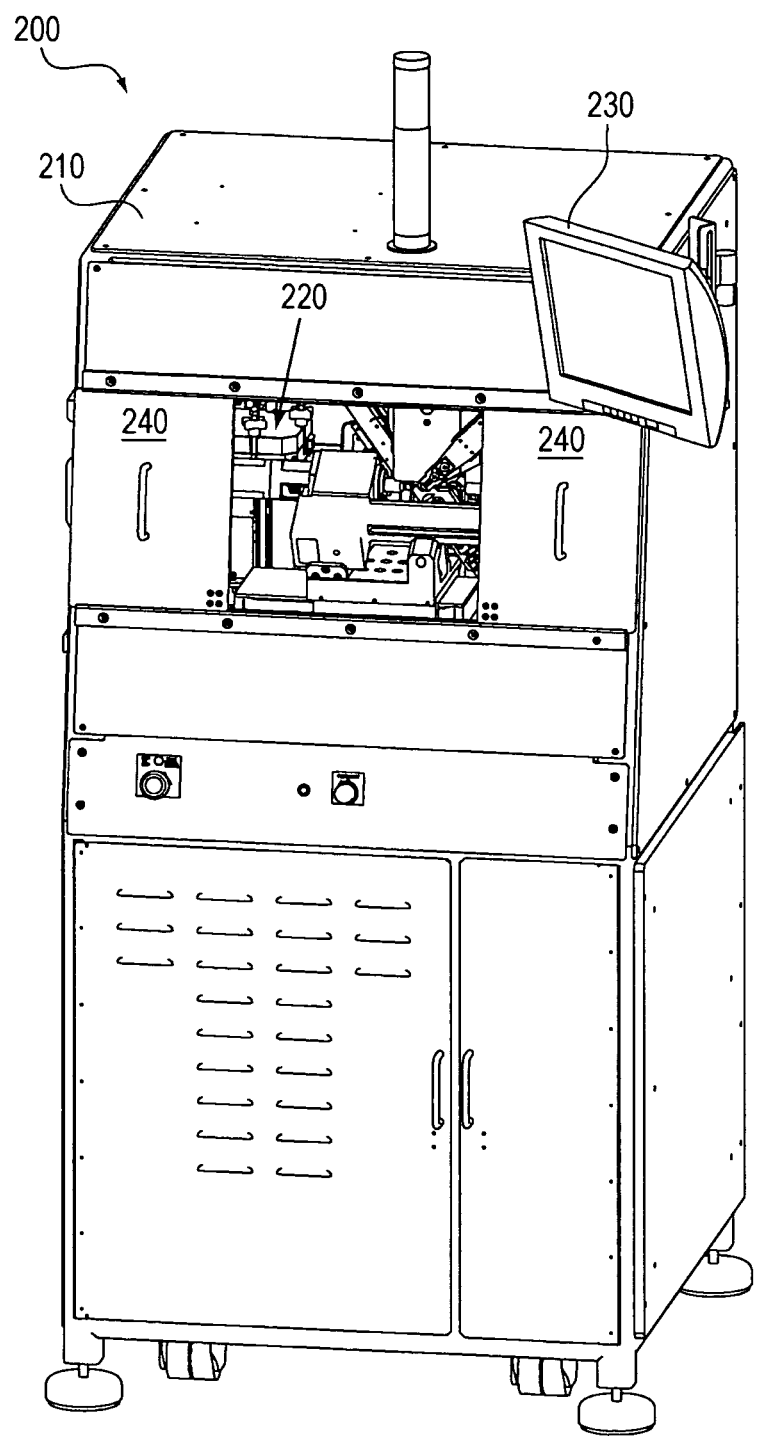
FIG. 2 illustrates a stent coating apparatus according to an embodiment of the invention.
Figure 3:
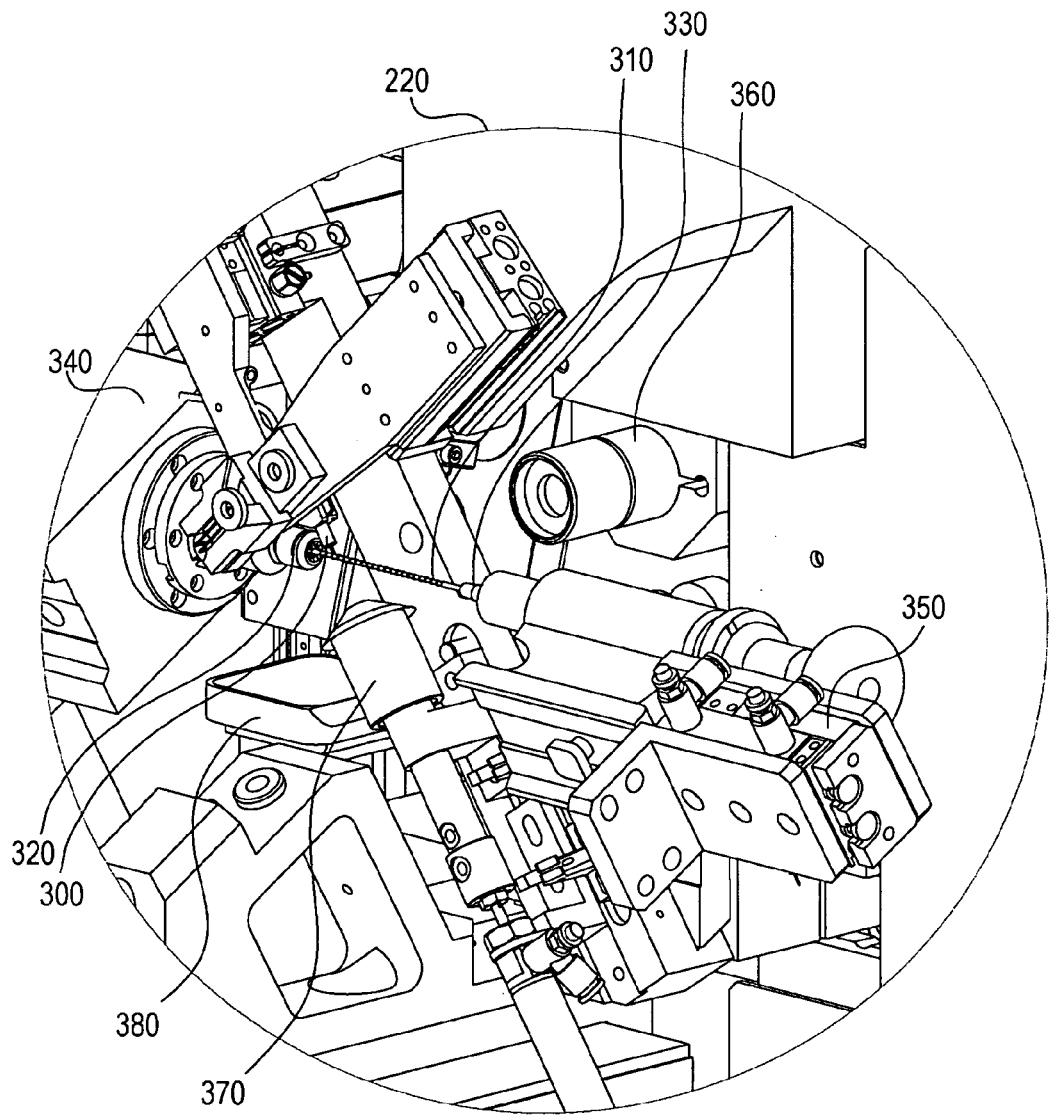
FIG. 3 and FIG. 4 illustrate the apparatus of FIG. 2 in further detail.
Figure 4:
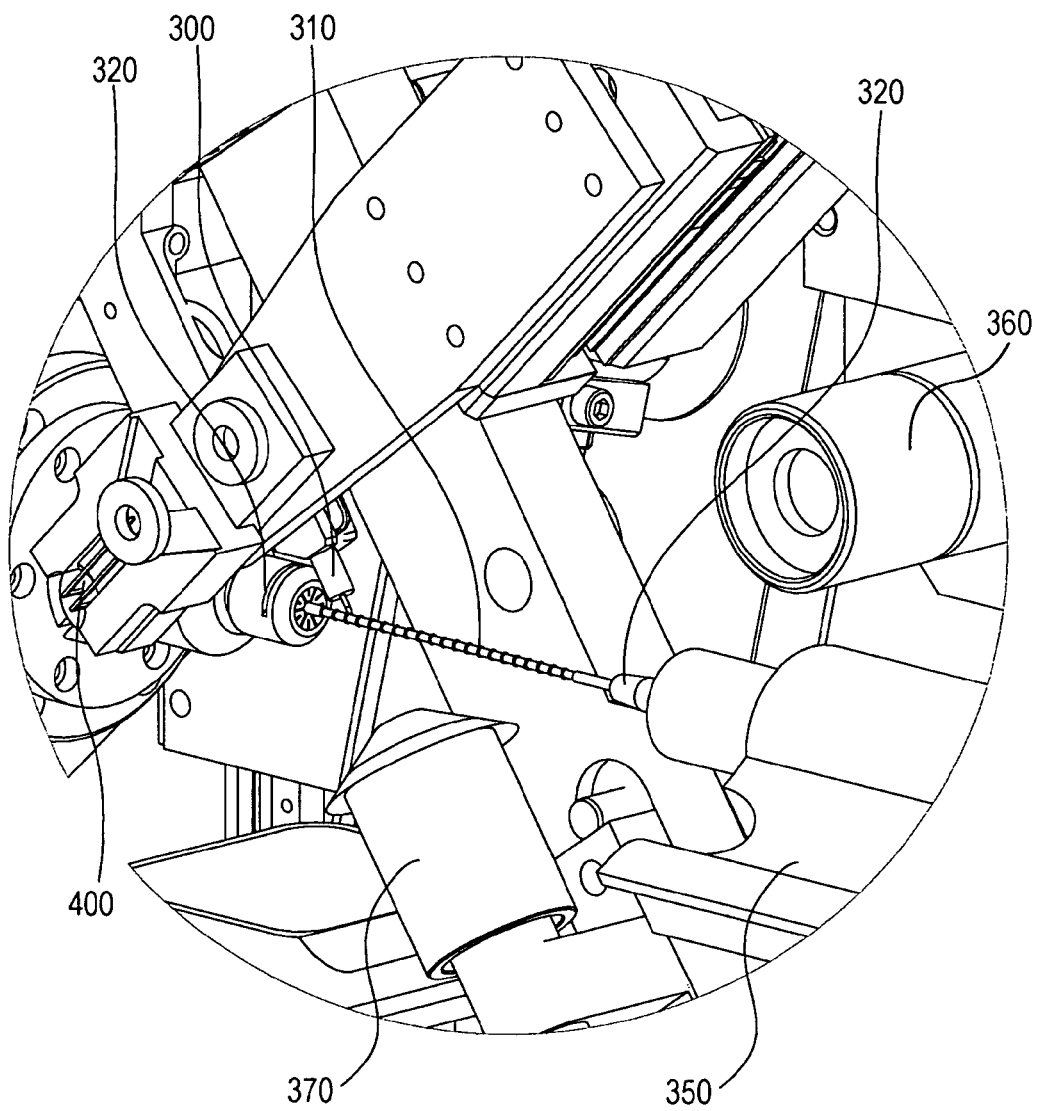

FIG. 2 illustrates a stent coating apparatus 200 according to an embodiment of the present invention. The apparatus 200 includes a casing 210 holding an electromechanical stent coating mechanism 220. The mechanism 220 can be accessed via sliding doors 240 located on a face of the casing 210. A touchpad monitor 230 is also coupled to the casing 210 and enables an operator to enter instructions for controlling the mechanism 220.

FIG. 3 to FIG. 7 illustrate the stent coating mechanism 220 in greater detail. The mechanism 220 may include a stent mandrel for supporting a stent 10 and a piezoelectric print head 300 for coating the stent 10. The mandrel 310 is supported by a collet 320 at a first end and by a support 330, such as a bearing support, at a second end. An electric motor 340 may be connected to the collet 320 to rotate the stent 10 about its longitudinal axis. A second electric motor 350 (see FIGS. 3 and 7) may be provided for linearly moving the mandrel 310 back and forth. The print head 300 may include a transducer that converts electrical energy into acoustic (vibrational) energy in the form of acoustic pulses. The acoustic energy ejects (or dispenses) droplets of the coating substance from the print head 300 onto the stent 10. Preferably, each acoustic pulse dispenses a single droplet from the print head 300.

Preferably, the mandrel is manufactured with sufficient precision and has sufficient dimensional stability, so that stent movement during coating operation is precise and predictable. Precise and predictable stent movement makes a precise coating of the stent possible. For example, the mandrel preferably is straight so as to limit the total indicated run out of the stent. Further, the mandrel diameter preferably is precise so that it is slightly less than the inner diameter of the stent. If the mandrel diameter is too small, the gap between the mandrel and the stent may cause the stent to move randomly during coating. If the mandrel diameter is too large, the stent inner surface may be damaged when the stent is mounted on the mandrel.

Preferably, carbide is used as the mandrel material to provide the mandrel with precise dimensions and dimensional stability over time and temperature. Since a carbide mandrel generally does not bend (it breaks instead of bending), the dimensional stability of an intact mandrel can be ensured. Additionally, a carbide mandrel can be machined without warping; this is difficult to do with many other materials because the mandrel is relatively thin and long.

Preferably, the mandrel has a color that facilitates the imaging of a mounted stent. For example, the mandrel may have a dark color, such as black, which provides a dark background for a light-colored stent. Or the mandrel may have, a light color, such as white, which provides a light background for a dark stent. This can be accomplished by using a dark or light-colored carbide. Alternatively, the mandrel may be coated with Teflon of a desired color. For example, a Teflon jacket of a desired color may be heat shrunk over the mandrel. Furthermore, a Teflon coating may provide a lubricious mandrel surface for a stent to slide on. This may facilitate the mounting of the stent on the mandrel and avoid or reduce damages to the stent inner surface.

Preferably, the contact between the inner surface of the stent and the outer surface of the mandrel is minimized or reduced. The surface contact between the stent and the mandrel may provide areas where a liquid coating substance can flow, wick, and collect as the coating substance is applied to the stent. As the solvent evaporates, the excess coating substance hardens to form excess coating at and around the contact points between the stent and the mandrel. Upon removal of the coated stent from the mandrel, the excess coating may stick to the mandrel, thereby removing some of the coating from the stent and leaving bare areas. Alternatively, the excess coating may stick to the stent, thereby leaving excess coating substance as clumps or pools on the stent.

Figure 5A:
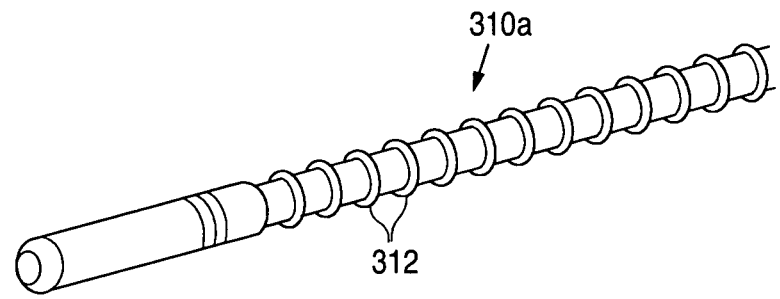
FIGS. 5a to 5c illustrate three embodiments for the stent mandrel of the apparatus of FIG. 2.
Figure 5B:
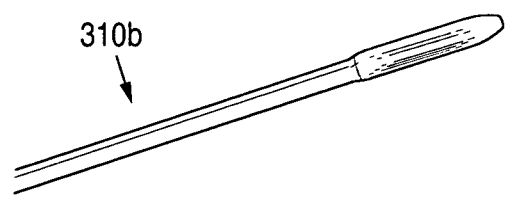
Figure 5C:
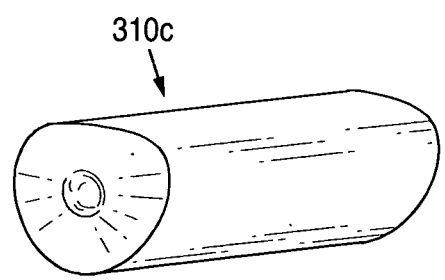
Figure 6:
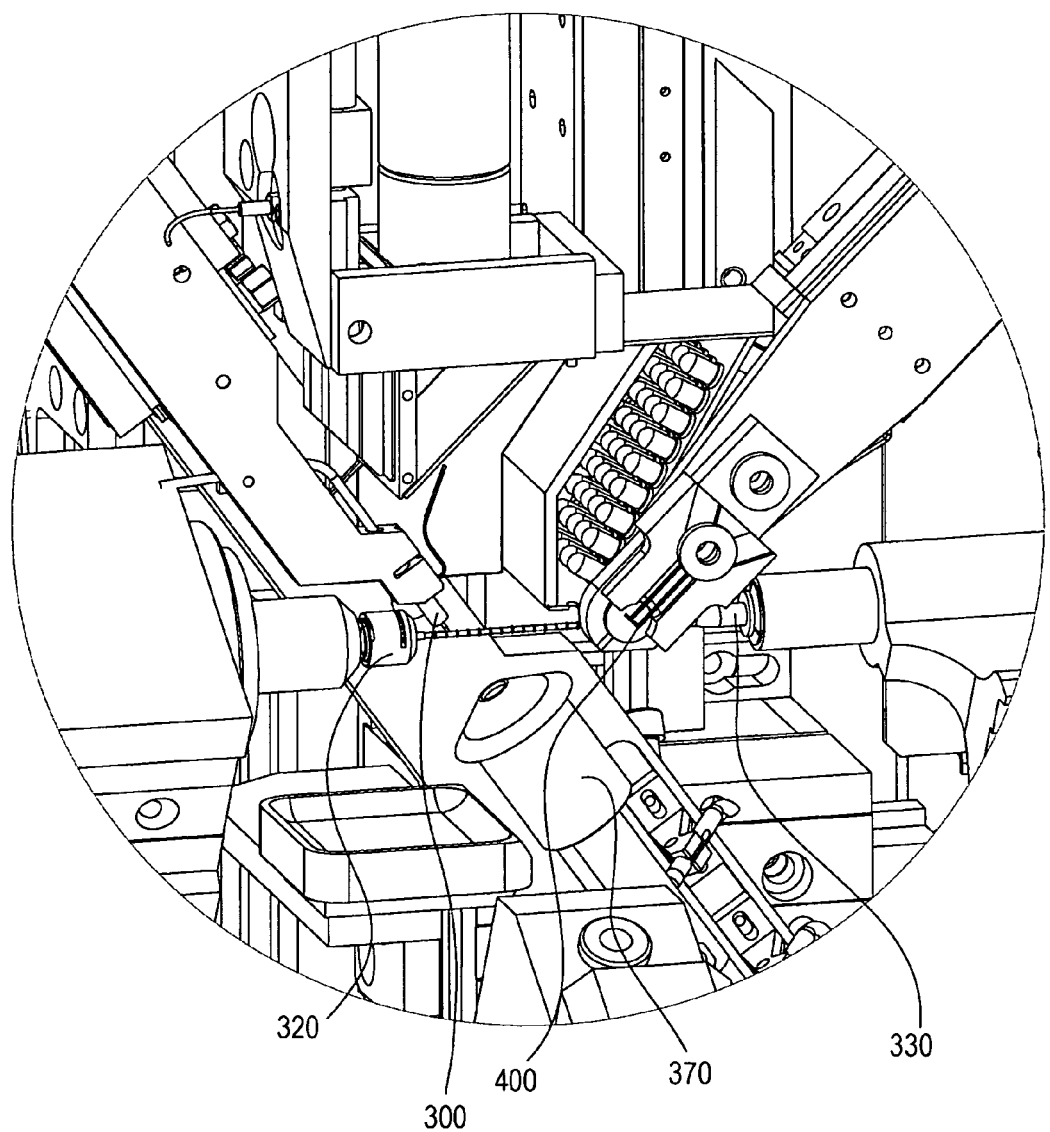
FIG. 6 illustrates the apparatus of FIG. 2 from a different angle.

The mandrel may be configured to minimize the surface contact between the stent and the mandrel so as to reduce areas of potential coating defects. FIG. 5a illustrates a mandrel 310a with circular protrusions 312 that are arranged along the longitudinal axis of the mandrel 310a. The spacing of the circular protrusions 312 matches the spacing of the stent rings. These circular protrusions 312 have line contact with the inner surface of the stent. In addition, the line contact is at the wide portion of the stent. The limited line contact at the wide portion of the stent geometry results in minimal coating defects. FIG. 5b illustrates a mandrel 310b with a triangular cross-section, and FIG. 5c illustrates a mandrel 310c with a cross-section having three lobes, although the cross-section may have more than three lobes. Each of the two mandrels 310b, 310c shown in FIGS. 5b and 5c has line contacts with the stent. Each of the three mandrels 310a, 310b, 310c may have a circumscribed diameter that is slight less than the inner diameter of the stent. Preferably, the circumscribed diameter of each mandrel 310a, 310b, 310c is 0.005 inches to 0.010 inches less than the inner diameter of the stent.

The print head 300 preferably is aligned with a stent strut 12 or connecting element 14 and coats each individual stent strut 12 or connecting element 14. Hereinafter, the term stent strut will also refer to connecting element for ease of discussion. The coating can be limited to just the outer surface of the strut 12. In some cases, the sidewalls of the struts 12 between the outer and inner surfaces can be partially coated. Partial coating of the sidewalls can be incidental, such as when some coating flows from the outer surface onto the sidewalls, or intentional.

The apparatus 200 may also include an imaging device 360 that images droplets generated by the print head 300. Preferably, the imaging device 360 is a camera, but another type of imaging device, such as a radar or an electron scanner, may be used. The apparatus 200 preferably includes a light 400, such as a strobe light, to illuminate the droplets. The images from the imaging device 360 can be used to confirm that the print head 300 did in fact emit a droplet and that droplet parameters meet certain requirements, such as requirements on volume, velocity, mode, and alignment with a stent strut.

The apparatus 200 may further include a controller that can determine droplet parameters from the images. The methods for determining droplet parameters from images are known and will not be described herein. The controller then compares the droplet parameters with the desired values and controls the print head 300 to adjust the droplet parameters towards the desired values. For example, if the droplets are too small or their velocity is too low, the controller can increase the ejecting power of the print head 300 to increase droplet volume or velocity. The ejecting power can be increased by increasing at least one of the width and magnitude of the acoustic pulses. On the other hand, droplet diameter decreases exponentially as pulse frequency increases.

The controller may also control other parameters of the print head 300 based on the droplet parameters. For example, the controller may control the ejection frequency to achieve a constant coating rate. If the droplet volume decreases, the droplet frequency may be increased to maintain a constant coating rate. For another example, the controller may stop coating one area and start coating another area when the first area has received a desired amount of coating. Whether the first area has received the desired amount of coating can be determined from the number of droplets applied to the area and the volume of each droplet.

The controller may further control the parameters of the print head 300 based on parameters other than droplet parameters. For example, the controller may control the ejection frequency based on the relative velocity between the stent surface and the print head 300 to achieve a substantially constant mount of coating per unit area of stent surface. In this example, the ejection frequency decreases when the relative velocity decreases around a complicated geometry, and the ejection frequency increases when the relative velocity increases on a more linear geometry.

Preferably, the aperture of the print head 300 has a diameter of less than about 20 microns, leading to droplets with a maximum diameter of about 20 microns. Alternatively, the aperture may have a diameter of about 10 microns to about 200 microns, yielding similar-sized droplets. Droplet volume can range from about 5 picoliters to about 30 picoliters. Pulse widths can vary from about 10 μsec to about 60 μsec. Preferably, the droplet velocity is about 4 to about 6 m/s, and firing accuracy is preferably about ±10 um.

Another imaging device 362 (see FIG. 6) may be used to control stent movement to keep the print head 300 aligned with the stent struts 12. The imaging device 362 may image the surface of the stent 10. Based on this image, the controller aligns the print head 300 with a stent strut 12 by causing the motors 340 and 350 to rotate and translate the stent 10 until alignment is achieved. The controller then causes the print head 300 to dispense coating substance. This camera 362 may also be used to align the droplet to the top-dead-center (TDC) of the stent for coating alignment. After a section of the stent has been coated, the motors 340 and 350 rotate and translate the stent 10 in relation to the print head 300 to position an uncoated section in front of the print head 300.

The apparatus 200 may include an illumination system for illuminating the stent for run out check and/or for scanning and coating visualization. In the illustrated embodiment, the illumination system includes a backlight 380 (FIG. 3) for illuminating the stent in silhouette for run out check and another light 382 (FIG. 6) for illuminating the stent for scanning and coating visualization. The imaging device 362 shown in FIG. 6 images the stent under illumination and the controller ensures that the stent 10 meets quality standards before the coating process. A stent may be rejected if it is damaged or if it wobbles during rotation, indicating a bend in the stent.

After the coating of the stent abluminal surface, the stent 10 can then have the inner surface coated via electrospraying or spray coating. Without masking the outer surface of the stent 10, both electrospraying and spray coating may yield some composition onto the outer surface and sidewalls of the stent 10. However, the inner surface would be substantially solely coated with a single composition different from the composition used to coat the outer surface of the stent 10. Accordingly, it will be appreciated by one of ordinary skill in the art that this embodiment enables the coating of the inner and outer surfaces of the stent 10 with different compositions. For example, the inner surface could be coated with a composition having a bio-beneficial therapeutic substance for delivery downstream of the stent 10 (e.g., an anticoagulant, such as heparin, to reduce platelet aggregation, clotting and thrombus formation) while the outer surface of the stent 10 could be coating with a composition having a therapeutic substance for local delivery to a blood vessel wall (e.g., an anti-inflammatory drug to treat vessel wall inflammation or a drug for the treatment of restenosis).

The apparatus 200 may include a tip cleaner 370 containing acetone or other cleansing agents. From time to time, such as before or after the coating of the stent 10, the print head 300 may touch the tip cleaner 370 via movement of the print head 300 or the tip cleaner 370. The cleaning agent helps remove coating substance that blocks the aperture of the print head 300.

Figure 7:
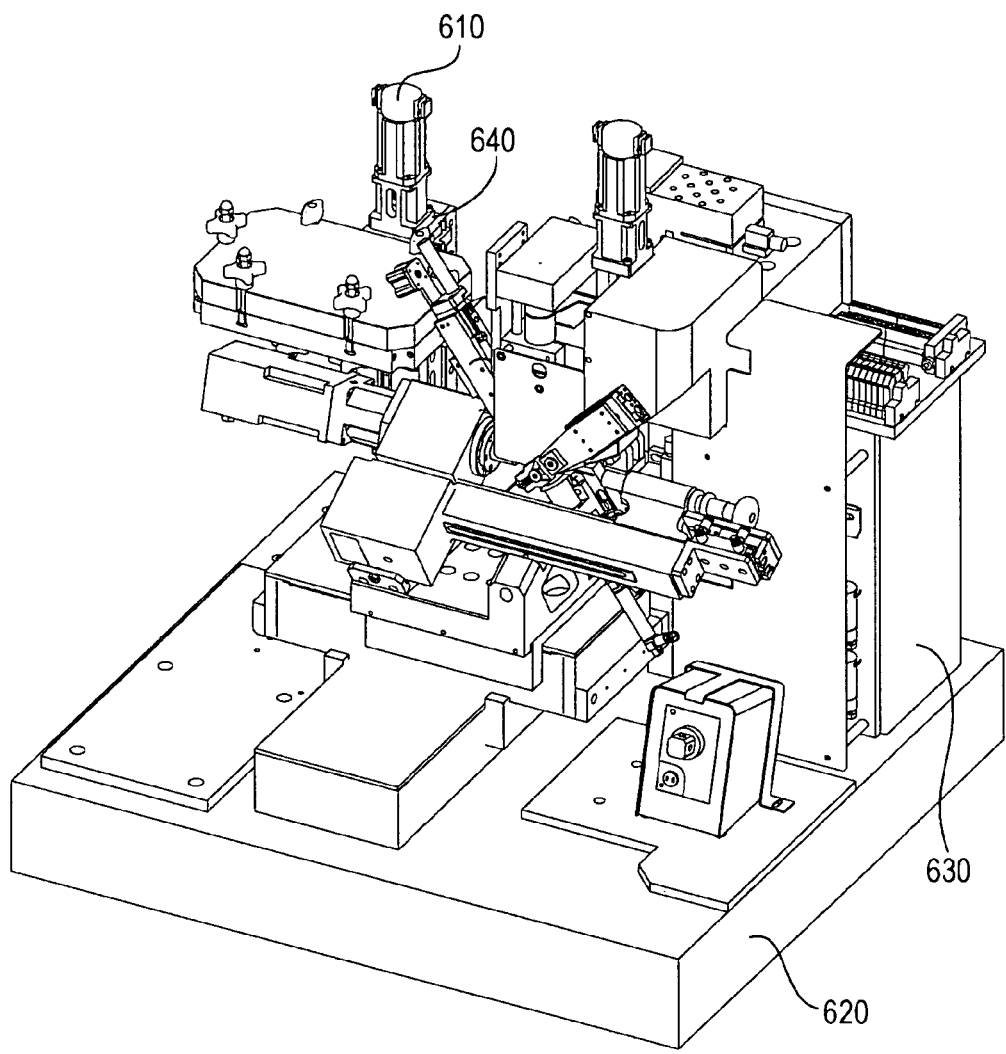
FIG. 7 illustrates the apparatus of FIG. 2 removed from a housing.

As shown in FIG. 7, the apparatus 200 preferably includes a reservoir 610 for holding a coating substance to be applied to the stent 10. The reservoir 610 is in fluid communication with the print head 300 and can dispense the coating substance to the print head 300 using gravity or pressure. The print head 300 generally has a small opening of 20 μm to 50 μm and therefore the coating substance does not exit the opening due to surface tension unless the transducer is activated. If the print head 300 is positioned underneath the stent 10 with the aperture pointing upwards, gravity can be used to form a negative or positive meniscus by placing the reservoir at a height above, even, or below the aperture. Further, the aperture may be coated with a low surface energy coating or any anti-wetting coating, such as TEFLON, to prevent coating from exiting the aperture except when desired. Preferably, the reservoir 610 is placed on an elevator 640, which adjusts the vertical positioning of the elevator 640 to balance the meniscus at the print head 300.

In an embodiment of the invention, the coating process can be continuous, i.e., the print head 300 can move along and coat the entire stent 10 without stopping, or move intermittently, i.e., coating a first section of the stent 10, stopping, and then aligning with a second section of the stent 10, and coating that second section. The second section may be adjacent to the first section or located a distance from the first section.

Preferably, the stent coating mechanism 220 is coupled to a granite mounting 620 and 630 beneath and behind the mechanism 220 for precision alignment component and vibration dampening. The granite mounting 620 and 630 may in turn be coupled to the casing 210.

Figure 8A:
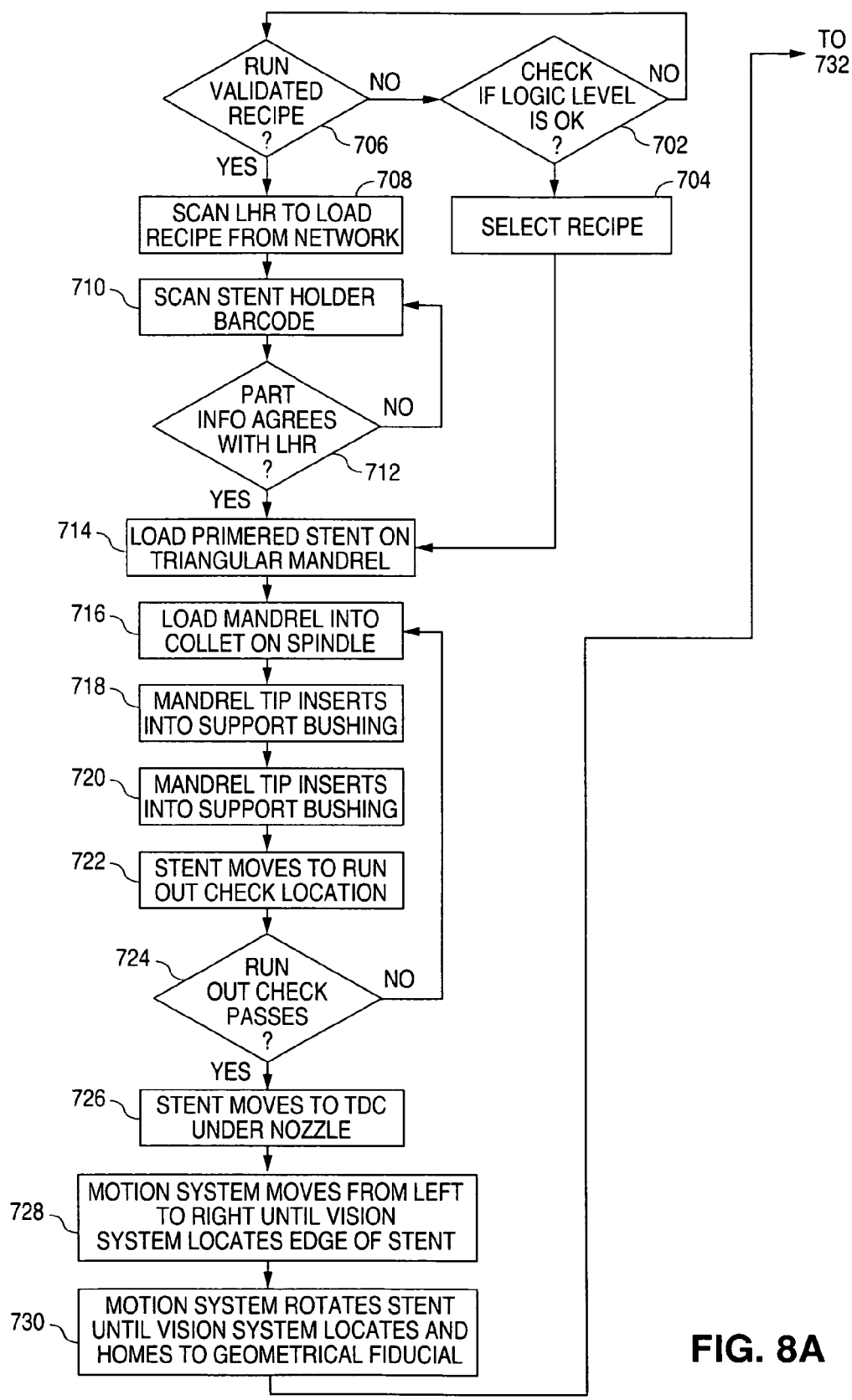
FIGS. 8A and 8B show a flowchart illustrating a method of coating an abluminal stent surface.
Figure 8B:
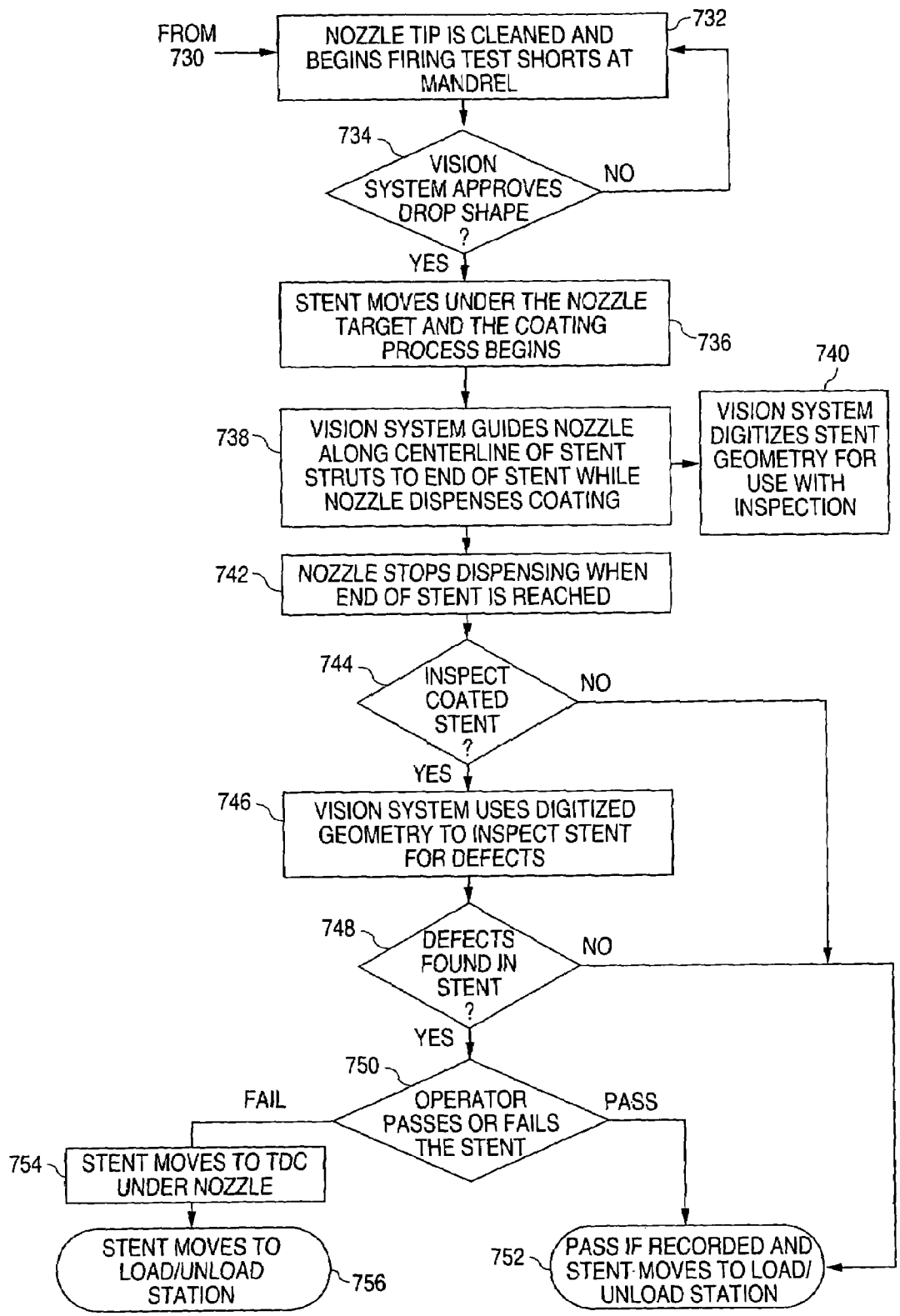

FIGS. 8A and 8B show a flowchart illustrating a method 700 of coating an abluminal stent surface. First, the operator's login level is checked (702). The operator's login level determines his or her level of access to the system. If the operator's login is accepted, then a recipe is selected (704) and a stent is loaded (714) on the mandrel 310. Otherwise, the lot history record (LHR) is scanned (708) to determine the recipe to use. The stent holder barcode is then scanned (710) and it is determined (712) whether the part information corresponding with the barcode agrees with the LHR. If there is no match, then the scanning (710) is repeated. Otherwise, the stent is loaded (714) on the mandrel 310. The mandrel 310 is then loaded (716) into the collet 320 and a recipe is initiated by pressing (718) a start button on the touchpad monitor 230. The mandrel tip is then inserted (720) into a support bushing (e.g., the support 330). The stent 10 is then moved (722) to a run-out check location for inspection, as discussed above.

If the run-out check does not pass (724), then the loading step (716) to the moving step (722) is repeated. Otherwise, the imaging device 362 may take an image of the stent, from which image a digitized coating path may be generated. The stent 10 is then moved (726) to the top dead center (TDC) under the print head 300. The motors 340, 350 move (728) from left to right until the controller locates the edge of the stent 10. The motors 340, 350 then rotate (730) the stent until the controller locates a reference point. The reference point may be a marking added to the stent or a natural feature of the stent that can be recognized by the controller. The print head is then cleaned (732) by being dipped in acetone and may eject (732) test droplets. During the test (732), the imaging device 360, as discussed above, may image the test droplets and determine if the test droplets meet the requirements.

If the test droplets do not meet the requirements, then the ejection (732) can be repeated. Otherwise, the stent 10 moves (736) under the print head 300 and the coating process begins. Based on the images provided by the imaging device 360, the controller uses the motors 340, 350 to guide (738) the print head 300 along the centerline of stent struts to the end of the stent while the print head 300 dispenses the coating. The print head 300 stops dispensing (742) when the end of the stent 10 is reached.

As an alternative to or in addition to taking an image of the stent prior to coating to determine the coating path, the image of the stent can be taken and the coating path can be determined during coating. Also, during the coating, the imaging device 360 can image the droplets, and the controller can determine if the droplets meet the requirements. If the droplets do not meet the requirements, the controller-adjusts the print head 300 as discussed above.

If the coated stent is not to be inspected (744), then a pass is recorded (752) and the stent 10 moves to a load/unload station. Otherwise, the controller inspects a digitized image of the coated stent for defects. If no defects are found (748), then a pass is recorded (752) and the stent 10 is moved (752) to a load/unload station. If defects are found (748), then the operator can pass or fail the coated stent. If passed, then the pass is recorded (752) and the stent moved to a load/unload station. Otherwise, the reason for failure is recorded (754) and the stent 10 is moved (756) to a load/unload station. The method 700 then ends.

The components of the coating substance or composition can include a solvent or a solvent system comprising multiple solvents, a polymer or a combination of polymers, a therapeutic substance or a drug or a combination of drugs. In some embodiments, the coating substance can be exclusively a polymer or a combination of polymers (e.g., for application of a primer layer or topcoat layer). In some embodiments, the coating substance can be a drug that is polymer free. Polymers can be biostable, bioabsorbable, biodegradable, or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

Representative examples of polymers that may be used include, but are not limited to, poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(D-lactic acid), poly(D-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Representative examples of polymers that may be especially well suited for use include ethylene vinyl alcohol copolymer (commonly known by the generic name EVOH or by the trade name EVAL), poly(butyl methacrylate), poly(vinylidene fluoride-co-hexafluororpene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

"Solvent" is defined as a liquid substance or composition that is compatible with the polymer and/or drug and is capable of dissolving the polymer and/or drug at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and mixtures and combinations thereof.

The therapeutic substance or drug can include any substance capable of exerting a therapeutic or prophylactic effect. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A method comprising:
ejecting a droplet of a coating substance towards a stent strut with a piezoelectric print head;
sensing a parameter of the droplet; and
determining whether the parameter of the droplet meets a requirement,
wherein the sensing includes taking an image of the droplet with an imaging device and determining the parameter from the image, wherein the parameter includes droplet alignment with the stent strut and the requirement includes a requirement on the droplet alignment with the stent strut, and wherein the coating substance is stored in a reservoir coupled to an elevator, such that movement of the elevator adjusts a meniscus of the coating substance in an aperture of the piezoelectric print head.

2. The method of claim 1, further comprising illuminating the droplet.

3. The method of claim 2, wherein the step of illuminating includes illuminating by a strobe light.

4. The method of claim 1, wherein the parameter includes droplet volume, and wherein the requirement includes a requirement on the droplet volume.

5. A method comprising:
ejecting a droplet of a coating substance towards a stent strut with a piezoelectric print head;
sensing a parameter of the droplet; and
determining whether the parameter of the droplet meets a requirement,
wherein the parameter includes droplet velocity, wherein the requirement includes a requirement on the droplet velocity, and wherein the coating substance is stored in a reservoir coupled to an elevator, such that movement of the elevator adjusts a meniscus of the coating substance in an aperture of the piezoelectric print head.

6. The method of claim 1, wherein the parameter includes droplet mode, and wherein the requirement includes a requirement on the droplet mode.

7. The method of claim 1, further comprising controlling the piezoelectric print head so that the parameter of the droplet meets the requirement.

8. The method of claim 1, further comprising adjusting ejecting power of the piezoelectric print head so that the parameter of the droplet meets the requirement.

9. The method of claim 1, further comprising adjusting at least one of pulse width and magnitude of the piezoelectric print head so that the parameter of the droplet meets the requirement.

10. The method of claim 1, further comprising adjusting ejection frequency of the piezoelectric print head so that the parameter of the droplet meets the requirement.

11. The method of claim 1, further comprising adjusting ejection frequency of the piezoelectric print head based on a relative velocity between a stent surface and the print head to achieve a constant amount of coating per unit area of stent surface.

12. The method of claim 1, further comprising adjusting acoustic frequency so that the parameter of the droplet meets the requirement.

13. The method of claim 1, further comprising adjusting stent position or print head position based on the determination of whether the parameter of the droplet meets the requirement.

14. The method of claim 1, wherein the determining is performed by a controller communicatively coupled to the piezoelectric print head.

15. The method of claim 5, wherein the determining is performed by a controller communicatively coupled to the piezoelectric print head.

16. The method of claim 5, wherein the sensing includes taking an image of the droplet with an imaging device and determining the parameter from the image.

17. The method of claim 16, further comprising illuminating the droplet.

18. The method of claim 17, wherein the step of illuminating includes illuminating by a strobe light.

19. The method of claim 5, wherein the parameter includes droplet volume, and wherein the requirement includes a requirement on the droplet volume.

20. The method of claim 5, further comprising controlling the piezoelectric print head so that the parameter of the droplet meets the requirement.

21. The method of claim 5, further comprising adjusting ejecting power of the piezoelectric print head so that the parameter of the droplet meets the requirement.

22. The method of claim 5, further comprising adjusting at least one of pulse width and magnitude of the piezoelectric print head so that the parameter of the droplet meets the requirement.

23. The method of claim 5, further comprising adjusting ejection frequency of the piezoelectric print head so that the parameter of the droplet meets the requirement.

24. The method of claim 5, further comprising adjusting ejection frequency of the piezoelectric print head based on a relative velocity between a stent surface and the print head to achieve a constant amount of coating per unit area of stent surface.

25. The method of claim 5, further comprising adjusting acoustic frequency so that the parameter of the droplet meets the requirement.

26. The method of claim 5, further comprising adjusting stent position or print head position based on the determination of whether the parameter of the droplet meets the requirement.

* * * * *